United States Patent [19]

Mayer et al.

[11] 4,229,382

[45] Oct. 21, 1980

[54] GLYCEROL PHOSPHITES ESTERIFIED WITH PHENOLCARBOXYLIC ACIDS

[75] Inventors: Norbert Mayer, Gablingen; Gerhard Pfahler, Augsburg; Franz Scheidl; Hartmut Wiezer, both of Gersthofen, all of Fed. Rep. of Germany

[73] Assignee: Hoechst Aktiengesellschaft, Fed. Rep. of Germany

[21] Appl. No.: 19,785

[22] Filed: Mar. 12, 1979

[30] Foreign Application Priority Data

Mar. 17, 1978 [DE] Fed. Rep. of Germany ....... 2811667

[51] Int. Cl.$^3$ .............................................. C07F 9/145
[52] U.S. Cl. .................................... 260/930; 260/923; 260/928; 260/937; 260/927 R; 546/25; 260/45.8 N; 260/45.85 B
[58] Field of Search ............... 260/928, 923, 937, 930; 546/25

[56] References Cited

U.S. PATENT DOCUMENTS

| | | | |
|---|---|---|---|
| 3,763,287 | 10/1973 | Chiddix et al. | 260/941 |
| 3,808,296 | 4/1974 | Brunetti | 260/937 |
| 4,096,114 | 6/1978 | Minagawa et al. | 546/25 |

*Primary Examiner*—Anton H. Sutto
*Attorney, Agent, or Firm*—Connolly and Hutz

[57] ABSTRACT

The invention provides novel esters of glycerol, in which one of the OH groups of the glycerol is esterified with a phenolcarboxylic acid, while the two other OH groups are esterified with phosphoric or phosphorous acid, substituted by long-chain alcohols, amines, mercaptans or phenol compounds. The products are suitable as light and heat stabilizers for plastics. They are distinguished by a high resistance to hydrolysis and extraction.

3 Claims, No Drawings

GLYCEROL PHOSPHITES ESTERIFIED WITH PHENOLCARBOXYLIC ACIDS

Phenol compounds or phosphites are used for a long time for stabilizing plastic materials, especially polyolefins.

As phosphite stabilizers, there are described also phosphites of glycerol (U.S. Pat. No. 3,082,189). However, these products were not able to be successfully marketed, probably because they are liquids of high viscosity being sensitive to hydrolysis, which can be added to the plastics and distributed therein homogeneously with great technical expenditure only.

Recently, attempts have been made to unite the phosphite function and the phenol function in one single stabilizer molecule as, for example, in the case of the esters of phenolcarboxylic acids and bicyclic pentaerythritol phosphite (German Offenlegungsschrift No. 2,219,695). These compounds, however, have the serious disadvantage of being sensitive to hydrolysis so that, due to normal atmospheric moisture, they lose their phosphite activity and the compatibility in the plastic material which is necessary for the phenol to become effective. Moreover, the ester interchange reaction of phenolcarboxylic acid esters with bicyclic pentaerythritol phosphite can be carried out with difficulty only, because the activity of the bases used as catalysts is reduced by reaction with the acidic phenols, so that the reaction proceeds very slowly. A similar behavior is observed in the case of mixed esters of phosphorus-containing acids, hydroxy-phenyl-substituted alcohols and aliphatic or aromatic alcohols (U.S. Pat. No. 3,763,287). These substances, too, have not succeeded hitherto on the market. Therefore, there is still a demand for phenol group-containing solid phosphites resistant to hydrolysis and obtainable in a simple and rapidly proceeding reaction.

Surprisingly, it has been found that glyerol phosphites esterified with phenolcarboxylic acids, in which radicals of long-chain alcohols, amines, mercaptans or phenol compounds are linked to the phosphorus, are sufficiently resistant to hydrolysis and meet furthermore the other requirements as to effectiveness and easy preparation.

The invention thus provides substances of the formula

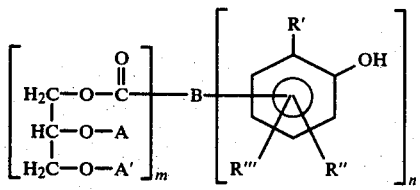

in which A and A' each are a monovalent radical of the structure

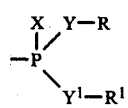

or, together, represent a monovalent radical of the structure

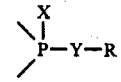

in which radicals

X is oxygen or no substituent;

Y is $-O-$, $-S-$ or $-NR''''-$ ($R''''=H$ or $C_1$ to $C_{20}$-alkyl);

R is a linear alkyl group having from 12 to 30 carbon atoms or, in the case of $Y=-O-$, alternatively a linear $\beta$-hydroxyalkyl group having from 12 to about 30 carbon atoms, or a 3-thia-5-hydroxyalkyl group having from 12 to about 32 carbon atoms, or a mono- or di-$C_{12}$ to $C_{30}$-fatty acid ester of the dihydroxypropyl radical; $-Y^1-R^1$ is either $-Y-R$ or a radical of the structures

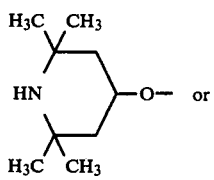

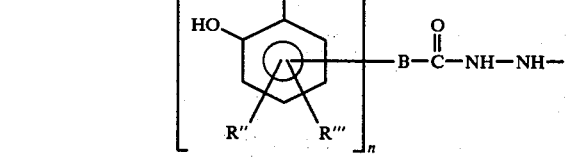

R', R'''' and R''', independently from each other, are H or $C_1$ to $C_4$-alkyl;

B is a chemical bond or (a) the radical of a linear or branched, unsubstituted or phenylsubstituted alkane having from 1 to 20 carbon atoms or (b) of an unsubstituted or $C_1$-$C_5$-alkylsubstituted cycloaliphatic alkane having from 5 to 12 carbon atoms, or (c) of an unsubstituted or $C_1$-$C_{12}$-alkylsubstituted aromatic hydrocarbon having 6 or 10 carbon atoms, or (d) a $-B'-O-B''$ group, or (e) a

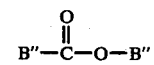

group; B' being a chemical bond or the radical of a linear, branched or cyclic, unsubstituted or phenylsubstituted alkyl having from 1 to 20 carbon atoms or of an unsubstituted or alkylsubstituted phenyl radical, and B'' being a chemical bond or a linear or branched alkyl radical having from 1 to 6 carbon atoms; and m and n each are either 1 or 2.

The above general formula indicates only the formal structure and the gross composition of the novel compounds, but it does not give defined details on the place of the phenolcarboxylic acid or phosphite ester bond at the glycerol molecule and the spatial arrangement of the substituents to one another.

The phenolic grouping of the above general formula stems from a phenol carboxylic acid of the following structure

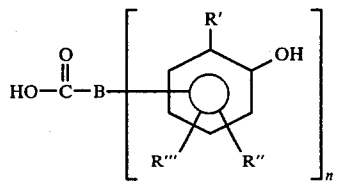

in which B, R', R'', R''' and n are as defined above. Such phenolcarboxylic acids, where n is 1, are for example salicylic acid, 3,5-di-tert.-butyl-4-hydroxy-benzoic acid, 3,5-di-tert.-butyl-4-hydroxy-phenylacetic acid, 3,5-di-tert.-butyl-4-hydroxy-phenylpropionic acid, or 2,4-di-tert.-butyl-3-hydroxy-6-methylbenzoic acid, as well as the derivatives thereof which are for example described in German Offenlegungsschrift No. 2,445,306.

Phenolcarboxylic acids where n is 2 are bis-hydroxyphenolcarboxylic acids such as described for example in German Offenlegungsschrift No. 2,544,014. Suitable are for example, 3,3-bis-(3'-tert.-butyl-4'-hydroxyphenyl)-butanoic acid, bis-(3-tert.-butyl-4-hydroxyphenyl)-acetic acid, bis-(3',5'-di-tert.-butyl-4'-hydroxyphenyl)-acetic acid, 2,2-bis-(3'-tert.-butyl-4'-hydroxyphenyl)-cyclohexanecarboxylic acid-(1), or 2,2-bis-(3'-tert.-butyl-4'-hydroxyphenyl)-cyclohexyl-1-propionic acid.

This class of compounds is preferred, especially bis-(3-tert.-butyl-4-hydroxy-phenyl)-acetic acid and 2,2-bis-(3'-tert.-butyl-4-hydroxy-phenyl)-butanoic acid.

Examples of hydroxyphenyldicarboxylic acids of the formula

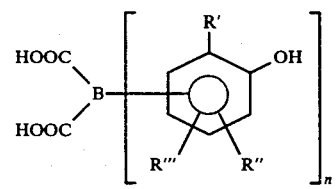

are 2-(3',5'-di-tert.-butyl-4'-hydroxy-phenyl)-malonic acid, 2,2-bis-(3'-tert.-butyl-4'-hydroxy-phenyl)-succinic acid or 2,2-bis-(3'-tert.-butyl-4'-hydroxy-phenyl)-glutaric acid.

Examples of ether group-containing phenolcarboxylic acids of the structure

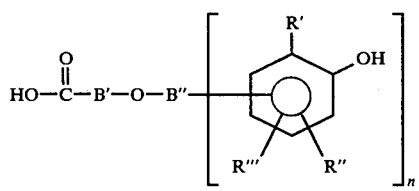

are 3-tert.-butyl-4-hydroxy-phenoxyacetic acid or p-(3-tert.-butyl-4-hydroxy-phenoxy)-benzoic acid.

Examples of ester group-containing phenolcarboxylic acids of the structure

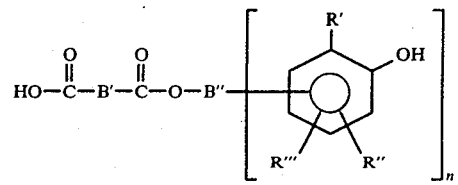

are the monoesters obtained by reaction of alkylated dihydroxy-benzenes with dicarboxylic acid derivatives, such as phthalic acid-mono-(3,5-di-tert.-butyl-4-hydroxyphenyl) ester, succinic or maleic acid-mono-(3,6-di-tert.-butyl-4-hydroxyphenyl) ester or terephthalic acid-mono-(2-hydroxy-3,5-di-tert.-butylphenyl) ester. Further examples are monoesters of dicarboxylic acids with the easily obtainable 3,5-di-tert.-butyl-4-hydroxybenzyl alcohol, 4-(m,m'-di-tert.-butyl-p-hydroxyphenyl)-butan-2-ol (German Offenlegungsschrift No. 2,309,375), 3-(3',5'-di-tert.-butyl-4'-hydroxyphenyl)-propanol and 3,3-bis-(3'-tert.-butyl-4'-hydroxyphenyl)-butanol.

The radicals —Y—R linked to phosphorus and represented by A and A' in the general formula stem from long-chain alkyl compounds of the formula H—Y—R, which contain a functional group with active hydrogen and may be for example α-β-diols of the structure R—CH(OH)—CH$_2$OH having a chain length of from 12 to 32, preferably of from 20 to 30 carbon atoms, or mixtures of such diols, which are obtained in a high yield by hydrolysis of the epoxide of long chain α-olefins; monoalcohols ROH having a chain length of from 12 to about 40 carbon atoms, for example fatty alcohols and wax alcohols, which may be obtained, for example, by hydrogenation of fatty and wax acids or which are present in natural and fossil waxes, or synthesis alcohols which may be obtained by oligomerization of ethylene and which are commercially available under the common name "afols". Stearyl and behenyl alcohols are preferred. Other preferred alcohol components are 3-thia-5-hydroxyalkyl alcohols with from 12 to about 32 carbon atoms, which may be obtained by addition of mercaptoethanol or thioglycerol to long chain epoxides, or a mono- or di-fatty acid or wax acid ester of glycerol, in which case the acid has a chain length of from 12 to about 40 carbon atoms; aliphatic primary mercaptans having from 12 to 30; preferably from 12 to 20, carbon atoms, for example octadecylmercaptan and dodecylmercaptan; and amines of the structure

in which R'''' is H or C$_{1-20}$-alkyl and R is C$_{12-30}$, preferably C$_{12-20}$alkyl, for example laurylamine, preferably stearylamine, N-methyl-stearylamine and distearylamine.

Compounds of the R'—Y'—H structure are the alcohol of formula (I) and hydrazines of formula (II)

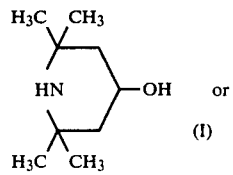

(I)

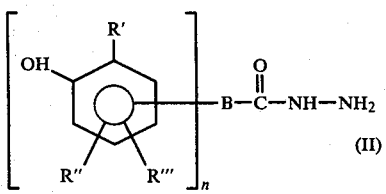

Compounds of formula (II) are described in German Offenlegungsschrift No. 2,711,206. Especially preferred are 3',5'-di-tert.-butyl-4'-hydroxyphenyl-propionic acid hydrazide and 3,3-bis-(3'-tert.-butyl-4-hydroxyphenyl)-butanoic acid hydrazide.

The phenolcarboxylic acid/glycerol esters serving as starting substances are prepared from phenolcarboxylic acids or the esters thereof with glycerol. Preferably, they are prepared by the rapidly and smoothly proceeding addition of phenolcarboxylic acids to glycide in the presence of a basic or acidic catalyst at temperatures of from about 50° to 150° C., especially 100° to 130° C., which proceeds according to the following scheme:

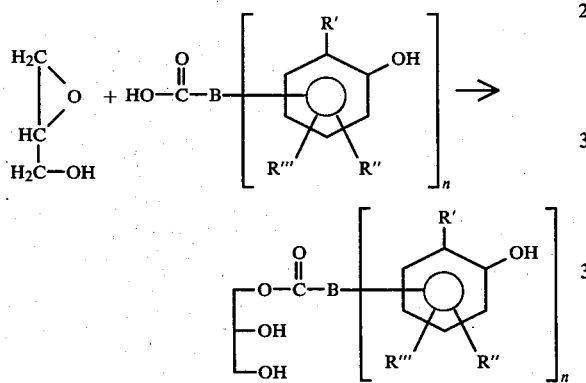

The reaction may be carried out without solvents, but alternatively in the presence of aromatic or aliphatic solvents such as toluene or di-isobutylketone, as described for example in German Offenlegungsschrift No. 2,449,847. Preferably and in accordance with this invention, the reaction is carried out in the melt of one of the above R—Y—H compounds, that is, long-chain alcohol, amine or mercaptan etc., or a mixture of these substances.

A special advantage of this preferred operation mode resides in the fact that after completed glycide addition, which takes from 30 minutes to 2 hours and the termination point of which can be clearly stated by thin-layer chromatography, ester interchange (and thus linkage with the R—Y—H compound serving as reactant in the addition reaction or the $R^1$—$Y^1$—H compound to be optionally added) can be carried out via phosphorus to obtain the final product by addition of a phosphorous acid or phosphoric acid ester with an easily volatile alcohol or phenol, while distilling off the alcohol set free, thus omitting the time-consuming and expensive posterior removal of a solvent. Therefore, the manufacturing process of the invention is a very simple and economic "one-pot" process.

Suitable phosphorus-containing starting compounds are generally derivatives of phosphoric acid and, preferably, of phosphorous acid containing readily volatile substituents which can be cleaved by alcoholysis, especially alcohol or amine substituents, for example, especially, trilower-alkyl or triaryl phosphites or phosphates, for example triphenyl phosphite, tripropyl phosphite, triethyl phosphate, trimethyl phosphate, and especially trimethyl and triethyl phosphite, or furthermore hexamethylphosphoric triamide or hexamethylphosphorous triamide. Optionally, $PCl_3$ or $POCl_3$ may be alternatively used.

The glycide addition is catalyzed by basic compounds, for example di- and trialkylamines, for example triethylamine and triisopropylamine, alkali metal alcoholates, alkali metal amides, hydrides and, preferably, alkali metal hydroxides, optionally also by acidic substances, such as ammonium salts. The catalyst ist added in an amount of from 0.01 to about 5%, calculated on the weight of the glycide.

The temperature of phosphite reaction is in the range of from 80° to 210° C., preferably of from 120° to 180° C. It is generally chosen such that the released alcohol distills off sufficiently rapidly. It is possible, of course, and in the case of high-boiling alcohols, for example phenol, even advisable, to support the cleavage of alcohol by operating under reduced pressure.

The amount of starting materials depends on what final products are to be obtained. Phenolcarboxylic acid and glycide are reacted with each other always in an about equivalent ratio. The phosphorus-containing component, the R—Y—H and $R^1$—$Y^1$—H components are used in such an amount that there is either 1 mol of R—Y—H compound and 1 mol of phosphorus-containing component per equivalent of the glycerol ester formed in the 1st process step, thus yielding cyclic phosphites, or per equivalent of glycerol ester there are used a total of 4 mols of the R—Y—H and $R^1$—$Y^1$—H components, with the proviso that at leat 1 mol of R—Y—H compound must be present, and are reacted with 2 mols of phosphorus-containing component, in which case open-chain glycerol ester diphosphites are obtained.

The final products solidify on cooling to wax-like solids which can be used as stabilizers without further purification, which is a special advantage. However, the products so obtained are not in every case chemically uniform substances and may contain by-products.

It is possible and in some cases advantageous to coat the products obtained with wax according to German Offenlegungsschrift No. 2,753,136 or to mix them with wax in the melt.

Apart from the fact that the products of the invention are easily obtainable, their extremely high resistance to hydrolysis in many cases must be stressed. This property was not to be expected because of the concentration of highly polar groups in a narrow molecular range, and the extremely high susceptibility to hydrolysis of a glycerol ester phosphite or phosphate.

The phosphorus-containing glycerol esters according to this invention are furthermore distinguished by the fact that they confer upon thermoplastic materials containing them a high stability to discoloration on processing, which is also surprising and was not to be expected, because glycerol esters, on thermal stress put to them, tend to formation of acroleine in a two-fold β-elimination reaction, which acroleine reacts with itself to give heavily discolored resins. This behavior is well known in the chemistry of fats, to which class tris-carboxylic acid-glycerol esters belong. It is all the more surprising that this expected phenomenon is not observed even at the elevated temperatures of plastics processing; on the contrary, an extremely effective stabilization to discoloration is found when using the compounds of the invention.

As compared to the commercial phenolic antioxidants, there is to be stressed furthermore the extraordinary resistance of the phenol compounds of the invention to extraction from the plastic material when it is contacted with oily or fatty substances. This property is of decisive importance, because on the one hand it ensures the intended protection of the plastic material against oxidation on contact with oils and fats, and on the other hand it prevents the especially undesirable contamination with the stabilizers of fatty or oily food possibly packaged in the plastic material.

The compounds of the invention increase the processing stability as well as the resistance to ageing by heat of plastics such as PVC and other chlorine-containing vinyl homo- or copolymers and especially alpha-olefin homo- or copolymers such as polyethylene, polypropylene or ethylene/vinyl acetate copolymers. They are used in amounts of from 0.005 to 5.0 parts by weight per 100 parts by weight of polymer.

In chlorine-containing plastics materials there are used as costabilizers in addition to the substances of the invention metal satls, epoxide stabilizers, polyols, or optionally alpha-phenylindole.

Known metal compound stabilizers in the present context are calcium, barium, strontium, zinc, cadmium, magnesium, aluminum and lead soaps of aliphatic carboxylic acids or of hydroxycarboxylic acids having approximately 12 to 32 carbon atoms, or of phenol-substituted aliphatic carboxylic acids, salts of such metals with aromatic carboxylic acids, for example benzoates, salicylates and (alkyl) phenolates, and organo-tin compounds, for example dialkyltin thioglycolates and carboxylates, as well as the analogous ester tin derivatives recently known. Known epoxide stabilizers are, for example, epoxidized soybean oil, tall oil, linseed oil, and epoxidized butyl oleate and the epoxides of long chain α-olefins.

Suitable polyols are for example pentaerythritol, trimethylol propane, sorbitol or mannitol, i.e. preferably alcohols having 5 or 6 carbon atoms and 3 to 6 hydroxyl groups.

A suitable stabilizer combination for the processing of halogen-containing plastics compositions consists, for example, of from 0.005 to 5, preferably from 0.05 to 3 and especially from 0.1 to 1, parts by weight of one or more phosphite compounds according to the present invention, from 0.1 to 10, preferably from 0.5 to 5, parts by weight of known metal compound stabilizers, from 0.1 to 10, preferably from 0.5 to 5, parts by weight of a known epoxide stabilizer and from 0 to 1 part by weight of a polyol, calculated on 100 parts by weight of polymer.

The compounds according to the present invention are also very efficient especially in the stabilization of polyolefins, so that this application is preferred. The addition of conventional amounts thereof (less than 1% by weight) to polypropylene considerably improves the stability to light and heat, especially in the presence of phenolic and optionally sulfidic antioxidants.

Phenolic and sulfidic stabilizers are intended to include the heat stabilizers generally used in plastics processing, for example 3,5-di-tert.-butyl-4-hydroxyphenyl-propionates, 2,5-di-tert.-butyl-p-cresol, alkylidene-bis-alkylphenols, esters and salts of bis-(4'-hydroxy-3'-tert.-butylphenyl)-butanoic acid or of cycloalkylidene-bis (alkylphenol)carboxylic acids or thiodipropionic acid esters of fatty alcohols or dioctadecyl sulfide and disulfide.

A stabilizer combination for use in the processing of halogen-free poly-α-olefins, for example high, medium and low pressure polymers of $C_2$ to $C_4$-α-olefins, especially polyethylene and polypropylene, or of copolymers of such α-olefins, consists for example, of from 0.01 to 2, preferably from 0.05 to 0.5, parts by weight of the calcium salt of a fatty acid or a wax acid, from 0.005 to 3, preferably from 0.01 to 1, parts by weight of a phenolic stabilizer, optionally 0.005, preferably from 0.01 to 1, part by weight of a sulfidic stabilizer and from 0.005 to 5, preferably from 0.05 to 1, part by weight of an organic phosphite, and from 0.005 to 5, preferably 0.05 to 1, parts by weight of one or more compounds of the present invention, for 100 parts by weight of polymer. If necessary, from 0.01 to 3 parts by weight of a special UV stabilizer can be added to the mixture. From among the large number of commercial UV stabilizers the following are named by way of example: alkoxyhydroxy-benzophenones, hydroxyphenyl-benzotriazoles, salicylic acid phenol esters, benzoic acid hydroxyphenol esters, benzylidenemalonic acid nitrile esters and so-called "quenchers" such as nickel chelates, hexamethylphosphoric acid triamide piperidine stabilizers known as hindered amine light stabilizers (HALS products) or the aza-adamantanes.

Mixtures of the compounds according to the present invention with known stabilizers improve the stability not only of polyolefins and of chlorine-containing polymers, but also of polyesters, polyamides, phenol-formaldehyde resins, epoxide resins, polyacrylonitrile, polycarbonate, polysiloxanes, polyethers, polyurethanes and styrenebutadiene rubber mixtures.

The following Examples illustrate the invention:

EXAMPLE 1

β-Hydroxytriacontyl-(3,5-di-tert.-butyl-4-hydroxybenzoyl)-glycerinyl-phosphite

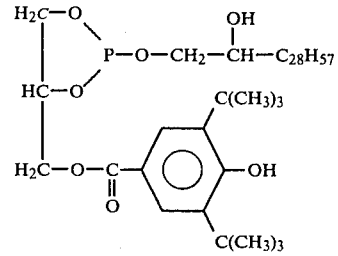

48 g (0,2 mol) 3,5-di-tert.-butyl-4-hydroxy-benzoic acid and 22.3 g (0.26 mol) glycide are stirred for 2 hours at 110° C. and under a nitrogen atmosphere in the presence of 0.1 g KOH and 100 g (0.2 mol) 1,2-dihydroxy-triacontane (obtained by hydrolysis of the $C_{30}$-epoxide prepared according to German Auslegeschrift No. 2,436,817, Examples 9 to 12) which in this process step has only the function of a reaction medium. After this time, no 3,5-di-tert.-butyl-4-hydroxy-benzoic acid can be detected any more by thin-layer chromatography. After having established a water jet vacuum in order to remove unreacted glycide, 34.8 g (0.105 mol) triethyl phosphite are added, and the ethanol set free from the reaction of phosphite with glycerol ester and the dihydroxy-triacontane is distilled off at 130° to 180° C. via a short Vigreux column in a slight nitrogen current, the bath temperature being adjusted in such a manner that the temperature at the distilling connecting tube does not exceed the boiling temperature of ethanol (78° C.).

After ethanol has ceased to develop, a vacuum is established in order to remove unreacted triethyl phosphite. Subsequently, the product in molten state is filtered through a heated pressure filter. 130 g of a wax having a flow/drop point of 86.5° to 87.5° C. are obtained.

EXAMPLES 2 to 12

In complete analogy to the operation mode as described in Example 1, compounds of the formula

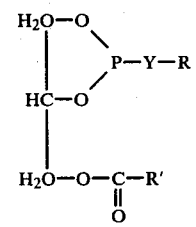

were prepared from 1 mol each of glycide, phenolcarboxylic acid, R—Y—H component and phosphite, the definition of R and R' resulting from the reactants listed in the following Table.

| Ex. No. | starting material R—Y—H | R'—COOH | Final product flow/drop point (°C.) |
|---|---|---|---|
| 2 | $C_{18}H_{37}$—OH | 2-hydroxybenzoic acid (salicylic acid): OH, COOH on benzene ring | 34/37 |
| 3 | $C_{18}H_{37}$—NH$_2$ | HO—[benzene with 2× X]—COOH (1) | 28/33 |
| 4 | $C_{18}H_{37}$—SH | {HO—[benzene with 2× X]—C(CH$_3$)—COOH}$_2$ (1) | 90/91.5 |
| 5 | $C_{28}H_{57}$—CHOH—CH$_2$OH | HO—[benzene with 2× X]—CH$_2$—CH$_2$—COOH (1) | 78/80 |
| 6 | $C_{28}H_{57}$—CHOH—CH$_2$OH | {HO—[benzene with 2× X]—CH—COOH}$_2$ (1) | 78/81 |
| 7 | $C_{18}H_{37}$—OH | {HO—[benzene with 2× X]—C(CH$_3$)—CH$_2$—COOH}$_2$ (1) | 42/45 |
| 8 | $C_{28}H_{57}$—CHOH—CH$_2$OH | {HO—[benzene with 2× X]—C(CH$_3$)—CH$_2$—COOH}$_2$ (1) | 81/85 |
| 9 | $C_{18}H_{37}$—OH | {HO—[benzene with 2× X]—C(CH$_3$)—CH$_2$—COOH}$_2$ (1) | 43/45 |

-continued

| Ex. No. | starting material R—Y—H | R'—COOH | Final product flow/drop point (°C.) |
|---|---|---|---|
| 10 | C$_{18}$H$_{37}$—OH | (HO—⌬—)$_2$CH$_2$—CH$_2$—COOH with cyclohexyl (1) | 46/48 |
| 11 | C$_{18}$H$_{37}$—OH | (HO—⌬—)$_2$C(CH$_3$)—(CH$_2$)$_3$—COOH (1) | 52/57 |
| 12 | C$_{18}$H$_{37}$—OH | (HO—⌬—)$_2$CH—C$_6$H$_4$—COOH (1) | 69/76 |

(1) + = C(CH$_3$)$_3$

EXAMPLES 13 to 27

Compounds of the formula

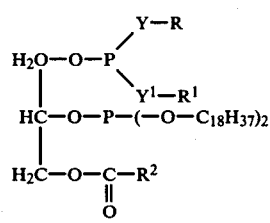

were prepared in analogy to Example 1. The definition of R, R$^1$ and R$^2$ results from the following Table.

There were used 1 mol each of phenolcarboxylic acid, glycide, R—Y—H and R$^1$—Y$^1$—H compound with 2 mols each of phosphite and stearyl alcohol.

| Ex. No. | starting material R—Y—H | R$^1$—Y$^1$—H | $R^2-\overset{O}{\underset{\|}{C}}-OH$ | Final product flow/drop point (°C.) |
|---|---|---|---|---|
| 13 | C$_{18}$H$_{37}$—OH | C$_{28}$H$_{57}$—CHOH—CH$_2$OH | OH-C$_6$H$_4$-COOH | 81/84 |
| 14 | C$_{18}$H$_{37}$—OH | C$_{28}$H$_{57}$—CHOH—CH$_2$OH | HO—⌬—COOH (1) | 72/73 |
| 15 | C$_{28}$H$_{57}$CHOH—CH$_2$OH | 2,2,6,6-tetramethyl-4-hydroxypiperidine (HN, OH, H$_3$C CH$_3$ / H$_3$C CH$_3$) | HO—⌬—COOH (1) | 69/71 |
| 16 | C$_{18}$H$_{37}$—OH | (HO—⌬—)$_2$C(CH$_3$)—CH$_2$—C(O)—NH—NH$_2$ | HO—⌬—COOH (1) | 43/45 |
| 17 | C$_{18}$H$_{37}$—OH | (HO—⌬—)$_2$C(CH$_3$)—CH$_2$—C(O)—NH—NH$_2$ | HO—⌬—CH$_2$—CH$_2$—COOH (1) | 72/75 |

-continued

| Ex. No. | starting material R—Y—H | R¹—Y¹—H | R²—C(=O)—OH | Final product flow/drop point (°C.) |
|---|---|---|---|---|
| 18 | $C_{18}H_{37}$—OH | (HO—Ar(+)₂—C(CH₃)—CH₂—C(=O)—NH—NH₂) | (HO—Ar(+)₂—CH—COOH) (1) | 78/78.7 |
| 19 | $C_{18}H_{37}$—OH | (HO—Ar(+)₂—C(CH₃)—CH₂—C(=O)—NH—NH₂) | (HO—Ar(+)₂—CH—COOH) (1) | 70/73 |

(1) + = $C(CH_3)_3$

| Ex. No. | R—Y—H | R¹—Y¹—H | R²—C(=O)—OH | Final product flow/drop point (°C.) |
|---|---|---|---|---|
| 20 | $C_{18}H_{37}$—OH | 2,2,6,6-tetramethyl-4-hydroxypiperidine (HN ring with H₃C,CH₃ gem-dimethyls and OH) | (HO—Ar(+)₂—CH—COOH) (1) | 36/37 |
| 21 | $C_{18}H_{37}$—OH | $C_{12}H_{25}$—SH | (HO—Ar(+)₂—CH—COOH) (1) | 30.5/31 |
| 22 | $C_{18}H_{37}$—OH | $C_{18}H_{37}$—OH | (HO—Ar(+)₂—C(CH₃)—CH₂—COOH) (1) | 38/40 |
| 23 | $C_{18}H_{37}$—OH | $C_{18}H_{37}$—NH₂ | (HO—Ar(+)₂—C(CH₃)—CH₂—COOH) (1) | 72/78 |
| 24 | $C_{18}H_{37}$—OH | $C_{28}H_{57}$—CHOH—CH₂OH | (HO—Ar(+)₂—C(CH₃)—CH₂—COOH) (1) | 79/80 |
| 25 | $C_{18}H_{37}$—NH₂ | $C_{18}H_{37}$—NH₂ | (HO—Ar(+)₂—(cyclohexyl)—CH₂—CH₂—COOH) (1) | 48/51 |
| 26 | $C_{18}H_{37}$—OH | $C_{18}H_{37}$—OH | (HO—Ar(+)₂—C(CH₃)—(CH₂)₃—COOH) (1) | 40/42 |
| 27 | $C_{18}H_{37}$—OH | $C_{28}H_{57}$—CHOH—CH₂OH | (HO—Ar(+)₂—CH(—C₆H₄—COOH)) (1) | 70.5/71 |

(1) + = —$C(CH_3)_3$

EXAMPLE 28

Di-stearyl-[2,2-bis-(3'-tert.-butyl-4'-hydroxyphenyl) glutaroyl]-bis-glycerinyl-diphosphite

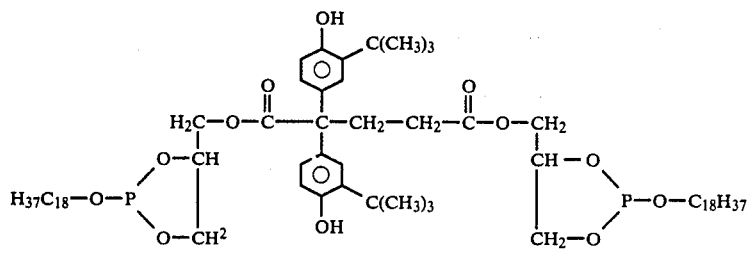

42,8 g (0,1 mol) 2,2-bis-(3'-tert.-butyl-4'-hydroxyphenyl)-glutaric acid, 20 ml (22,3 g=0.26 mol) glycide and 0.05 g KOH are stirred in 100 ml toluene for 90 minutes at 100° C. under a nitrogen blanket. The toluene is then distilled off, and 36 ml (=35 g=0.21 mol) triethyl phosphite are added, after which the inner temperature is raised to 110° C. As soon as ethanol begins to develop, 34 g (0.2 mol) stearyl alcohol are added, and the ethanol set free is distilled off at 150°–180° C. via a short Vigreux column in the manner as described in Example 1.

The product obtained has a flow/drop point of 34°/35° C.

EXAMPLE 29

62-Hydroxytriacontyl-hepta-stearyl-[2,2-bis-3'-tert.-butyl-4'-hydroxy-phenyl)-glutaroyl]-bis-glycerinyl-tetraphosphite

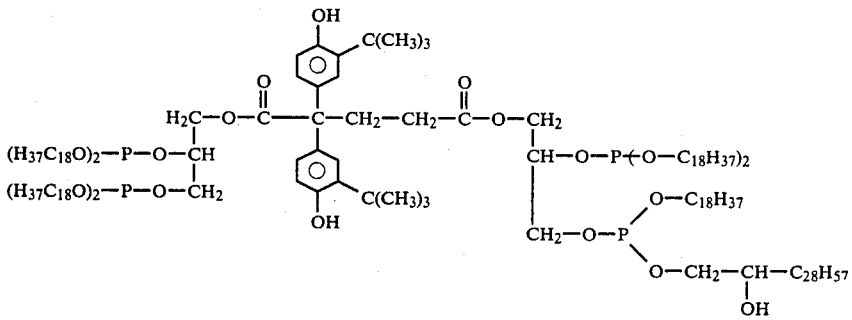

42,8 g (0,1 mol) 2,2-bis-(3'-tert.-butyl-4'-hydroxyphenyl)-glutaric acid, 20 ml (=22.3 g=0.26 mol) glycide and 0.05 g KOH are stirred in 100 ml toluene for 90 minutes at 100° C. under a nitrogen blanket. Subsequently, the toluene is distilled off and 72 ml (=70 g=0.42 mol) triethyl phosphite are added, while the inner temperature is maintained at about 110° C. As soon as ethanol begins to develop, 189 g (0.7 mol) stearyl alcohol and 50 g (0.1 mol) 1,2-dihydroxytriacontane are added, and the ethanol set free is distilled off at 130°–180° C. in the manner as described in Example 1.

The product obtained has a flow/drop point of 64°/65° C.

EXAMPLE 30

β-Hydroxytriacontyl-hepta-stearyl-[2,2-Bis-(5'-tert.-butyl-4'-hydroxy-malonyl]-bis-glycerinyl-tetraphosphite

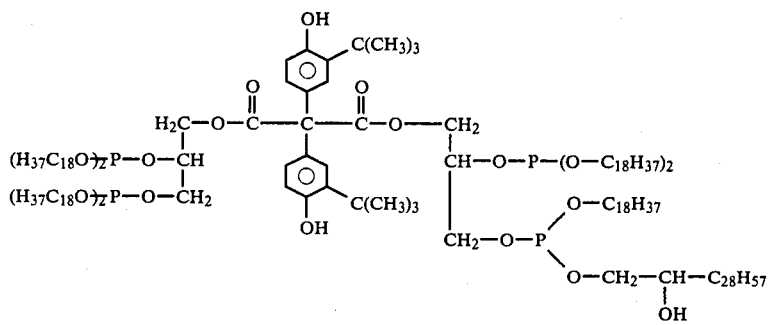

2.00 g (5 mmol) 2,2-di-(3'-tert.-butyl-4'-hydroxyphenyl)-malonic acid and 1 ml (10 mmols) glycide are stirred for 90 minutes in 5 ml toluene in the presence of a trace of KOH at 100° C. and under a nitrogen blanket. The toluene is distilled off, 3.6 ml (20 mmols) triethyl phosphite are added to the residue, and the temperature is raised to about 110° C. As soon as ethanol begins to develop, 9.45 g (35 mmols) stearyl alcohol and 2,50 g (5 mmols) 1,2-di-hydroxy-triacontane are added, subsequently the batch is stirred with progressive temperature raise to about 160° C. until the development of ethanol has ceased. Reduced pressure is established for a short time, and the batch is then allowed to cool. The product obtained has a flow/drop point of 61°/61.5° C.

EXAMPLE 31

This example is intended to show the surprisingly high stability to hydrolysis of the phosphites according to the invention, which is examined in the following manner: 5 g each of the respective phosphite are boiled for 20 minutes in 100 ml of deionized water. The mixture is then allowed to cool, the aqueous phase is filtered off through a folded filter, and from the filtrate, two samples each of 20 ml are pipetted off and titrated with 0.1 N KOH against bromophenol blue.

In the following table is indicated the degree of hydrolysis determined under these conditions, as quotient of the actual consumption of KOH and the theoretically possible consumption of KOH with a complete hydrolysis. For comparative purposes, the stability to hydrolysis of other phosphites known as stabilizers was determined.

| Phosphite according to Ex. No. | Hydrolysis degree after 20 minutes boiling (in % of theory) |
| --- | --- |
| 1 | 28 |
| 5 | 3 |
| 6 | 29 |
| comparative substances: | |
| di-stearyl-pentaerythrityldiphosphite | 55 |
| triphenyl phosphite | 84 |
| trisnonylphenyl phosphite | 57 |
| diphenyl-isooctyl phosphite | 55 |

EXAMPLE 32

This Example is to show the stabilizing action of the phenol group-containing phosphites of the invention (the parts indicated are by weight). On a two-roll mill, a mixture of

- 100 parts of unstabilized polypropylene powder, having a density of 0.90 and a melt flow index i₅ of about 6 g/10 min (determined according to ASTM D 1238-62 T),
- 0.5 part of 3,5-di-tert.-butyl-4-hydroxyphenyl-propionic acid stearyl ester and
- 0.10 part of one of the compounds of the invention is homogenized for 5 minutes at 200° C. Subsequently, the molten plastic material is molded at 200° C. to form a plate having a thickness of 1 mm. Strip-shaped test specimens (100×10×1 mm) are cut from the cold plate, which specimens, in order to determine the resistance to ageing by heat, are suspended on a motor-driven rack with rotating hurdles in a drying cabinet with air circulation and subjected to a temperature of 140° C. at steady and uniform feed of fresh air. The time after which the specimens begin to become brittle (according to DIN 53 383 characterized by the formation of discolored, turbid spots partially peeling off) is recorded. The test results are listed in the following Table:

| Compound acc. to Example No. | residence time in days |
| --- | --- |
| 1 | 29 |
| 4 | 35 |
| 6 | 37 |
| 19 | 42 |
| without (comparison) | 15 |

As the Table shows, the substances of the invention are excellent stabilizers for polyolefins.

What is claimed is:

1. Compounds of the formula

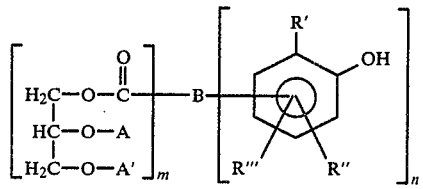

in which A and A' each are a monovalent radical of the structure

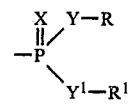

or, together, represent a monovalent radical of the structure

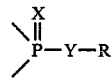

in which radicals

X is oxygen or no substituent;

Y is —O—, —S— or —NR''''—(R''''=H or $C_1$ to $C_{20}$-alkyl);

R is a linear alkyl group having from 12 to 30 carbon atoms or, in the case of Y=—O—, alternatively a linear β-hydroxyalkyl group having from 12 to about 30 carbon atoms, or a 3-thia-5-hydroxyalkyl group having from 12 to about 32 carbon atoms, or a mono- or di -$C_{12}$ to $C_{30}$-fatty acid ester of the dihydroxypropyl radical;

—Y¹—R¹ is either —Y—R or a radical of the structures

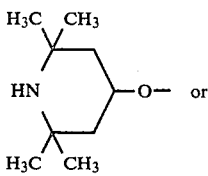

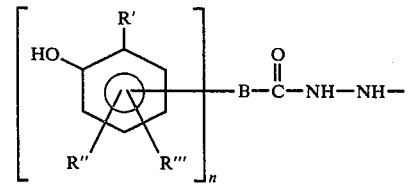

R', R" and R''', independently from each other, are H or $C_1$ to $C_4$-alkyl;

B is a chemical bond or (a) the radical of a linear or branched, unsubstituted or phenylsubstituted alkane having from 1 to 20 carbon atoms or (b) of an unsubstituted or $C_1$-$C_5$-alkylsubstituted cycloaliphatic alkane having from 5 to 12 carbon atoms, or (c) of an unsubstituted or $C_1$-$C_{12}$-alkylsubstituted aromatic hydrocarbon having 6 or 10 carbon atoms, or (d) a —B'—O—B" group, or (e) a

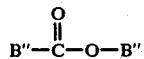

group; B' being a chemical bond or the radical of a linear, branched or cyclic, unsubstituted or phenylsubstituted alkyl having from 1 to 20 carbon atoms or of an unsubstituted or alkylsubstituted phenyl radical, and B" being a chemical bond or a linear or branched alkyl radical having from 1 to 6 carbon atoms; and m and n each are either 1 or 2.

2. Compounds as claimed in claim 1, wherein X is no substituent, Y is —O—, R stands for a linear alkyl or β-hydroxyalkyl radical having from 12 to 30 carbon atoms, —Y¹—R¹ is —Y—R, and the hydroxyphenylcarboxylic acid radical has the following structure

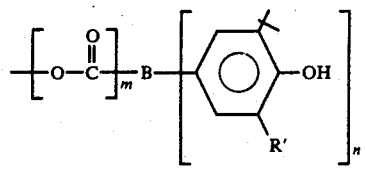

in which B, R', m and n are as defined in claim 1.

3. Compounds as claimed in claim 2, wherein the hydroxyphenylcarboxylic acid radical has the structures

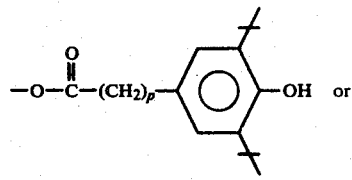

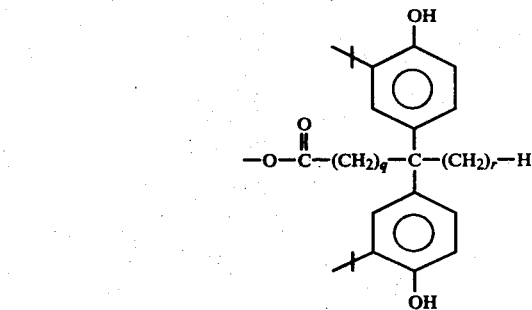

in which p, q each are zero, 1, 2 or 3, and r is zero or 1.

* * * * *